(12) United States Patent
Tondello et al.

(10) Patent No.: US 7,948,626 B2
(45) Date of Patent: May 24, 2011

(54) METHOD FOR THE AUTOMATED MEASUREMENT OF GAS PRESSURE AND CONCENTRATION INSIDE SEALED CONTAINERS

(75) Inventors: Giuseppe Tondello, Padua (IT); Massimo Fedel, Padua (IT)

(73) Assignee: Universita degli Studi di Padova, Padua (IT)

( * ) Notice: Subject to any disclaimer, the term of this patent is extended or adjusted under 35 U.S.C. 154(b) by 94 days.

(21) Appl. No.: 12/447,542

(22) PCT Filed: Oct. 24, 2007

(86) PCT No.: PCT/IT2007/000743
§ 371 (c)(1),
(2), (4) Date: Apr. 28, 2009

(87) PCT Pub. No.: WO2008/053507
PCT Pub. Date: May 8, 2008

(65) Prior Publication Data
US 2010/0067012 A1    Mar. 18, 2010

(30) Foreign Application Priority Data

Oct. 30, 2006    (IT) .............................. TO2006A0778

(51) Int. Cl.
*G01N 21/39*    (2006.01)

(52) U.S. Cl. ........................................ 356/437; 356/432

(58) Field of Classification Search .......... 356/432–444; 73/705, 700; 250/559.4, 343, 437, 339.01, 250/339.13
See application file for complete search history.

(56) References Cited

U.S. PATENT DOCUMENTS

| | | | | |
|---|---|---|---|---|
| 4,834,535 | A * | 5/1989 | Cammann | 356/307 |
| 5,407,638 | A * | 4/1995 | Wang | 422/82.09 |
| 5,621,213 | A * | 4/1997 | Barshad | 250/373 |
| 5,813,767 | A * | 9/1998 | Calabro' et al. | 374/142 |
| 6,121,627 | A * | 9/2000 | Tulip | 250/559.4 |
| 6,356,350 | B1 * | 3/2002 | Silver et al. | 356/437 |
| 6,597,462 | B2 * | 7/2003 | Kramer et al. | 356/519 |
| 6,639,678 | B1 * | 10/2003 | Veale | 356/437 |
| 6,853,452 | B1 * | 2/2005 | Laufer | 356/436 |
| 7,222,537 | B2 * | 5/2007 | Lehmann et al. | 73/705 |

* cited by examiner

*Primary Examiner* — Sang Nguyen
(74) *Attorney, Agent, or Firm* — Bryan W. Bockhop; Bockhop & Associates, LLC

(57) ABSTRACT

The device comprises a laser source which emits a beam of a predetermined wavelength towards an optically transparent closed container and detectors arranged to detect the laser beam which is attenuated by the gas absorption. The detectors provide the first data of absorption representative of a first absorption spectrum of the gas including distorted absorption lines and noise. The invention implements a method of calculation aimed at receiving and elaborating said first data. The output of the operation are parameters that represent a second absorption spectrum free of noise and distortion in the absorption lines. From these parameters we are able to determine the gas pressure and concentration in the container.

11 Claims, 13 Drawing Sheets

METHOD FOR THE AUTOMATED MEASUREMENT OF GAS PRESSURE AND CONCENTRATION INSIDE SEALED CONTAINERS

FIELD OF THE INVENTION

This invention relates to a method and to an apparatus that measures pressure and concentration of a gas in sealed containers and has been specifically designed for use with bottles (e.g. of wine). It employs an innovative method for determining the pressure and concentration of the gas in the head space of the container by measuring its absorption spectrum.

BACKGROUND ART

The ability to measure the total pressure within a sealed container, as well as the concentration of a particular gas in the container, is very important in several fields, ranging from the drug industry to food production. In the wine industry, for example, the ability to take a precise measurement of the concentration and pressure of carbon dioxide inside bottles (but without damaging either the bottle or its contents in any way) has several important applications: it is useful for distinguishing between champagne and sparkling wine (which have different allowable levels of carbonation); for monitoring the state of conservation of a single bottle; and even for fine-tuning the equipment used in the bottling process. Similarly, in the pharmaceutical and food packaging sectors (e.g. lyophilized components) the determination of the oxygen content is critical as an indicator of the conservation state of the product and of the integrity of the container.

At present, the methods commonly used for these kinds of pressure measurements include electronic pressure or vacuum gauges; pressure-measuring cells based on ceramic technology; piezoresistive sensors, etc. However, all of these methods share the disadvantage of being invasive, because in order to measure the gas present in a given container they need to extract a sample, and thereby spoil the integrity of the container's cork or seal. Moreover these methods are difficult to integrate as on-line controls in the production process.

For sparkling wine, for example, the current standard instrument for measuring above-atmospheric pressure is the aphrometer, which functions by piercing the bottle's cork or seal and measuring the total pressure inside. Unfortunately, the aphrometer is not able to measure the concentration of individual gases (such as carbon dioxide) or the partial pressure of the gases that comprise the total atmosphere within the bottle. This is an important shortcoming, because regulations regarding certain kinds of wine production distinguish between the partial pressure from carbon dioxide and the total pressure within the bottle (that can be due also to the contribution of other gases like nitrogen and oxygen). As such, it is clear that the aphrometer is not an adequate instrument.

In recent years, some novel measuring techniques for the detection of oxygen have been developed based on optical or opto-acoustic methods such as absorption spectroscopy in the modality TDLAS (Tunable Diode Laser Absorption Spectroscopy) or FMS (Frequency Modulation Spectroscopy). These systems have been studied for applications in the pharmaceutical sector, where a production-line control is required on any single piece. However, these systems have been limited to the detection of oxygen, and need reference container for calibration. A typical system is described by Veale et al. (U.S. Pat. No. 6,639,678 B1) which shows a system using derivative spectroscopy applied to the detection of pressure inside transparent containers and with predetermined background detection and calibration.

In contrast, we propose an apparatus to measure the pressure of the gas inside a generic bottle made of glass or other partially optically transparent materials, where the optical properties, such as absorption and scattering, are completely unknown. In this case the background absorption must be reconstructed. A novel calculation method that allows the self-referenced determination of the measured quantity, being it the pressure or the concentration, is disclosed. Our invention offers a method for measuring in real time (i.e. during the bottling filling phase and the conservation period) the pressure and the concentration inside a sealed container without reference container for calibration. Furthermore, this is accomplished by means of a measuring system that is simple, easy to operate, and usable both on the bottling lines as well during after-production controls, by using a spectroscopic method well known as the TDLAS spectroscopy.

These and others purposes are achieved by the invention with a measuring method and implementation whose main characteristics are described in the claims paragraph.

BRIEF DESCRIPTION OF THE FIGURES

The present invention is further described in the detailed description which follows, in reference to the noted plurality of drawings by way of non-limiting examples of preferred embodiments of the present invention, and wherein.

DETAILED DESCRIPTION OF THE INVENTION

Figure 1:
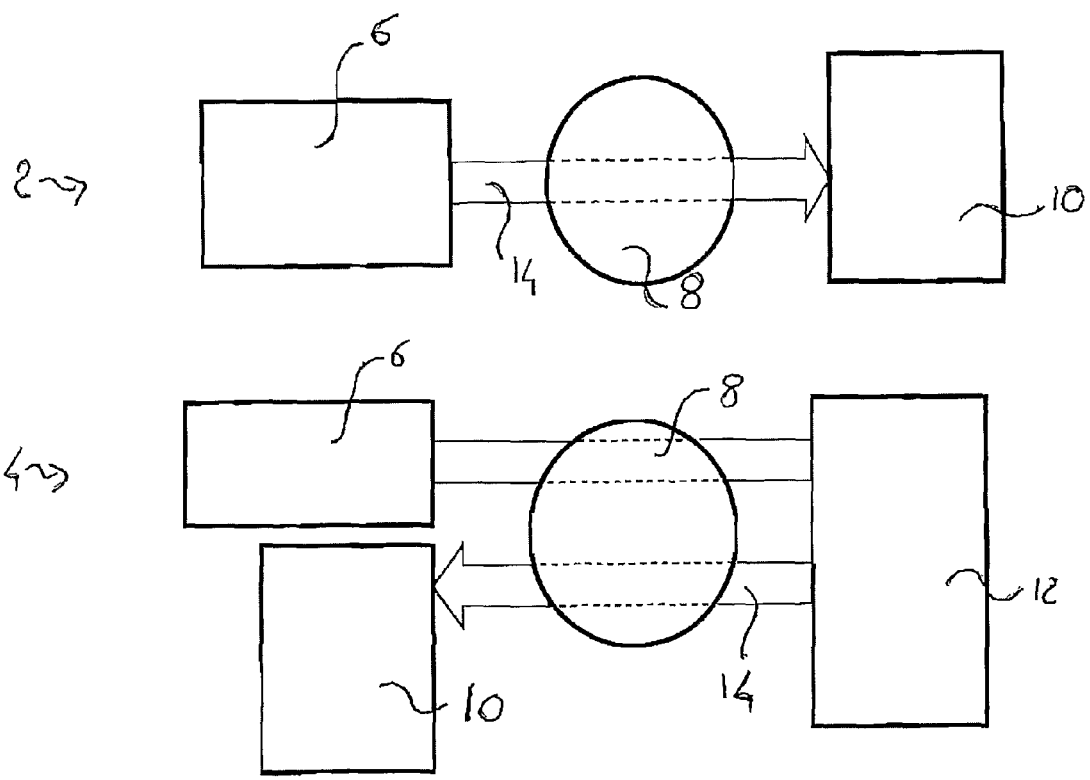
FIG. 1 is a block schematic view of two possible configuration of the measuring system according to the present invention.

FIG. 1 shows two possible configurations: 2 and 4 are schematic diagrams of a measuring system for absorption spectroscopy. In the first configuration: 2 there is a laser source 6, a container 8, that is the object of the measurement and a detector 10. In the second configuration 4 identical objects are indicated by same numbers ed in addition there is a retro-reflecting optic 12. Such retro-reflecting optic 12 can be as way of example a mirror, a corner cube or simply a diffusive screen. Differently from the first configuration 2, the source 6 and the detector 10 are located from the same size with respect to container 8.

For both configurations 2 and 4 there is the possibility of including two lenses, not indicated in FIG. 1, in the optical path represented by the arrow 14; the first lens is a collimating lens and the second one a collecting lens. These lenses can be standard plano-convex lenses as well as grin lenses. The latter ones have a greater width than the former and have the purpose of both collimating the beam and of reducing the optical path in free space, thereby minimizing the passage of the beam towards gas molecules present in the path external to the region of interest.

Also cylindrical lenses could be used with the purpose of correcting the optical aberrations introduced by the surface of the container 8; this is important in the case in which container 8 is e.g. a champagne bottle with thickness of the walls as large as 5-8 mm and mainly of cylindrical shape. In respect to the type of container 8 means of regulating the respective position of the lenses as well as other optoelectronic devices could be included. They are not shown in the figure.

The measuring system is based on the physical principle that different elements in the gas phase present absorption at different frequencies, or lines in the electromagnetic spectrum. Such frequencies being characteristics of the particular gas. These absorption lines have approximately a Lorentzian shape with a width as a known function of the pressure. The contribution due to the Doppler effect is in general quite small (for pressures above atmospheric pressure) and can be neglected.

In particular the gas object of the measure present in container 8 produces an absorption of the beam coming from laser source 6 according to the Lambert-Beer law:

$$I(v, x) = I_0(v) e^{-\tau(v,x)} \quad (1)$$

Where I is the intensity as measured by detector 10, $I_0$ the intensity impinging on the container 8 and $\tau$ is the optical depth given by:

$$\tau(v) = C \cdot x \cdot \sigma(v) \quad (2)$$

in which C is the concentration of the gas present in container 8, x is the length of the absorbing material and $\sigma(v)$ is the molecular absorption cross-section, function of the wave-number v (expressed in $cm^{-1}$). Both x and $\sigma(v)$ are known quantities, therefore the optical depth can be determined with a simple measure on the object under test. Furthermore it is known that the absorption cross-section presents a constant shape (Lorentzian) whose characteristics parameters (amplitude, width as function of the pressure and center point) can be derived form several spectroscopy data base and are constant even while other parameters of the measure vary. This behaviour allows the determination of the quantity C, by a comparison between the quantities I and $I_0$ for several molecules of interest depending on the availability of a suitable laser source 6. The main molecules interesting this invention are carbon dioxide and oxygen as they are of interest in the case when the container 8 is a bottle of wine. In any case it is possible to realize the measure also with reference to water vapour.

Figure 2A:
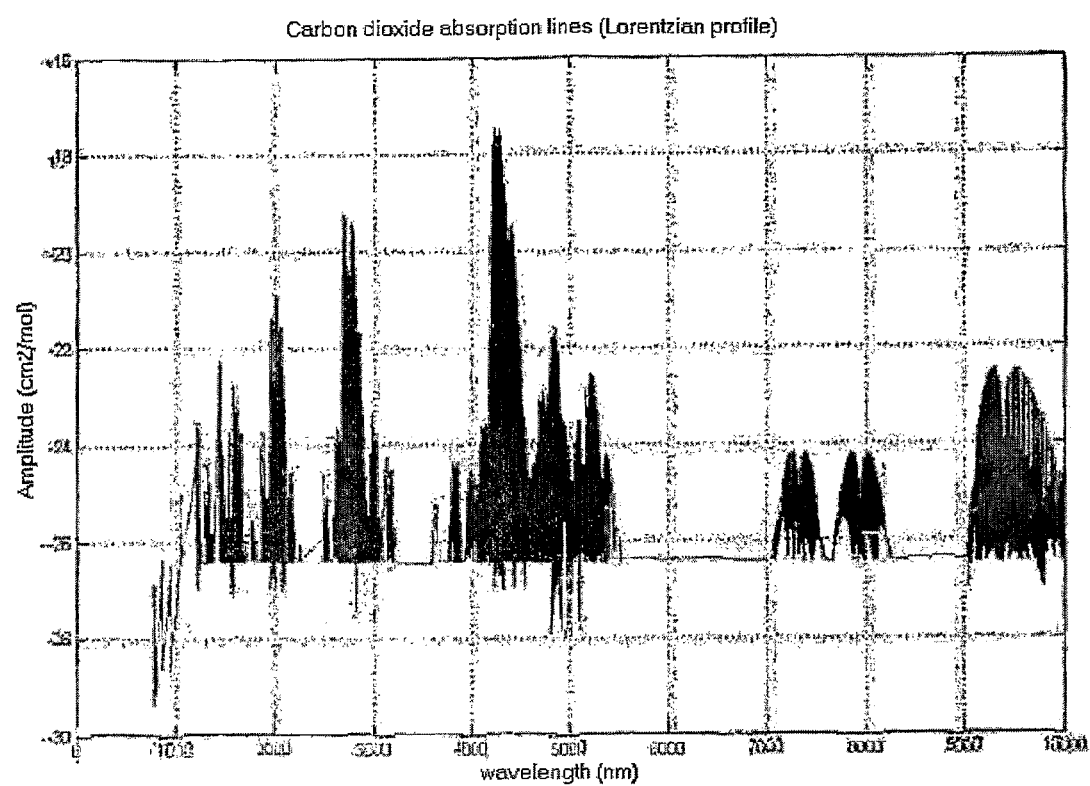
FIGS. 2(A) through 2(D) show a graphical representation indicating carbon dioxide absorption spectra at different wavelength intervals and different pressure.
Figure 2B:
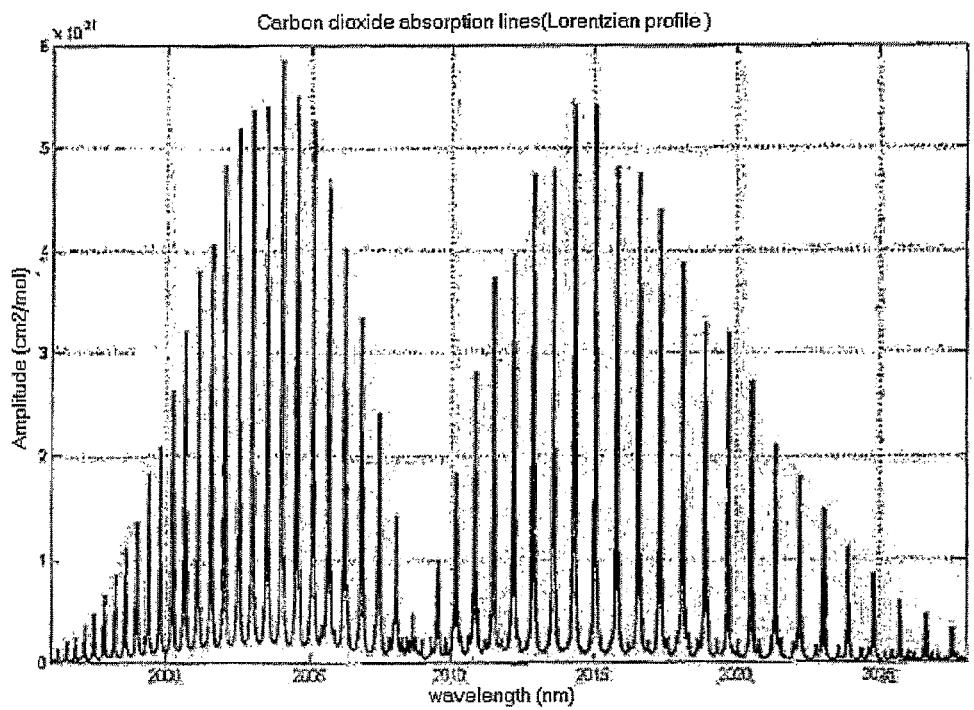
Figure 2C:
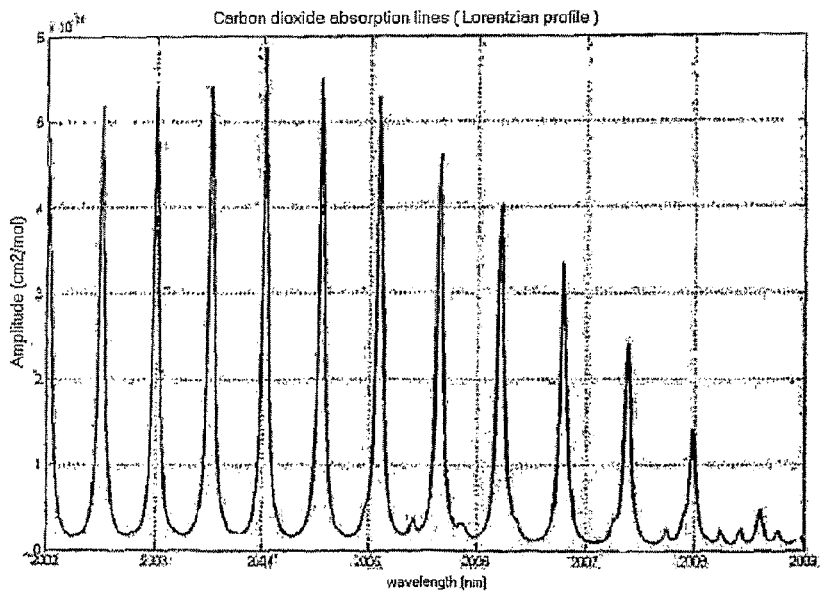
Figure 2D:
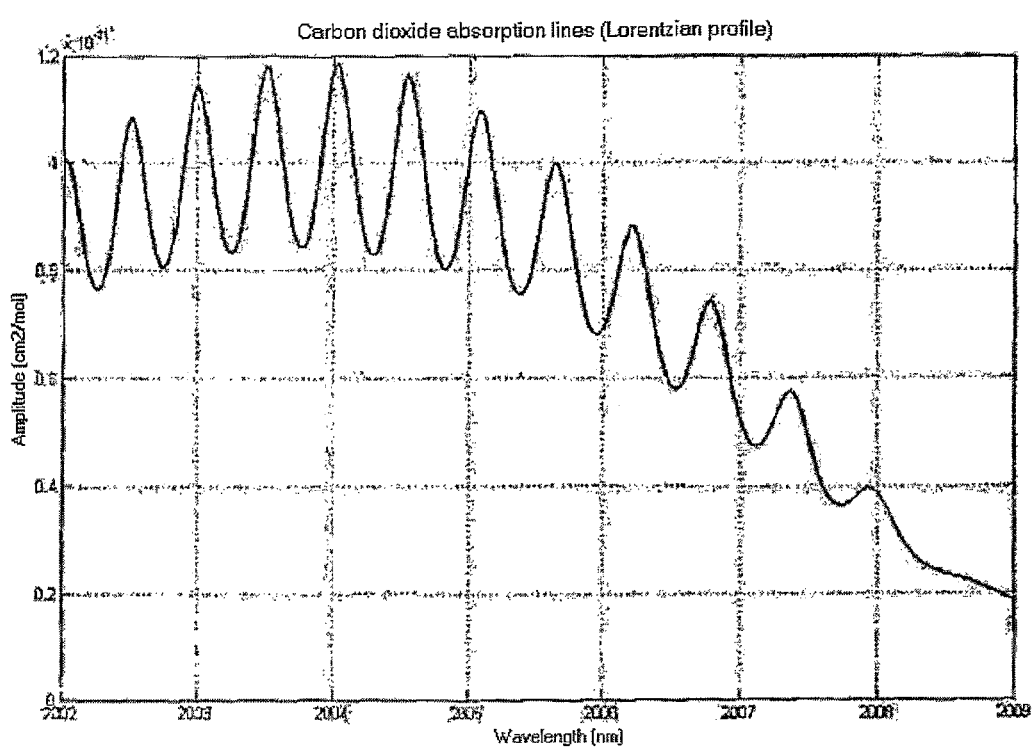
Figure 3:
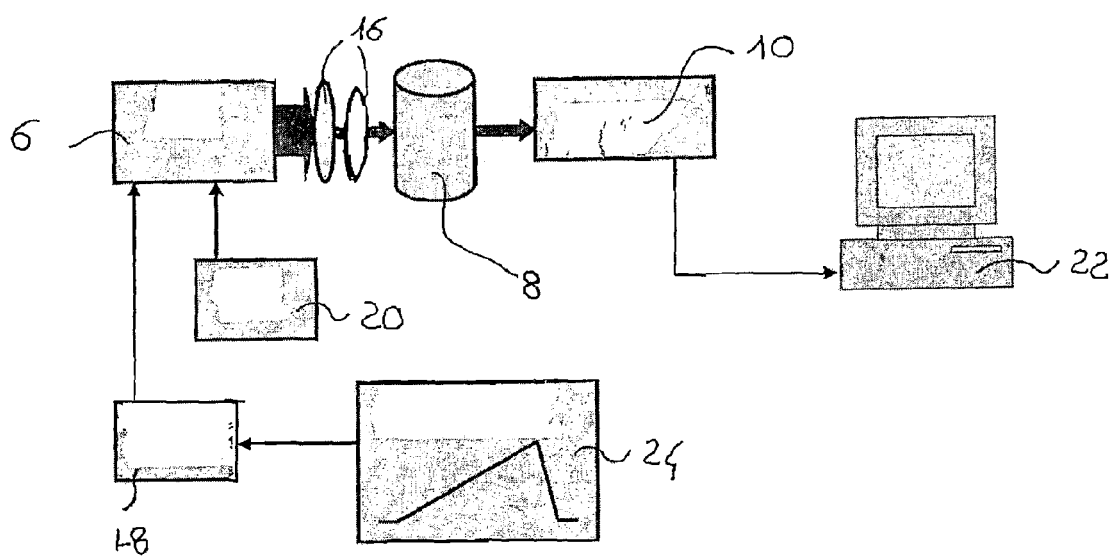
FIG. 3 is a working scheme of the device.

It is possible to increase the sensitivity using laser sources 6 emitting in the spectral regions where the molecule of interest has the greatest absorption. In particular laser source 6 emitting at wavelengths exciding 2 μm is preferable as in this spectral region there are some strong absorption lines as shown in FIGS from 2a to 2d. In FIG. 2a the absorption spectrum of carbon dioxide at atmospheric pressure and in the interval 0-10 μm is shown; FIG. 2b shows an enlargement of said spectrum in the region around 2 μm. In FIGS. 2c and 2d are shown the absorption spectra in a possible region of measurement i.e. in the interval 2002-2009 nm respectively for the atmospheric pressure and at a pressure of 7 bar. Scanning the chosen line is realized by modulating the wavelength emitted by the laser. Consequently for this type of analysis can be used any laser source 6 whose wavelength can be tuned and of spectral width smaller than the absorption line. Among the laser sources 6 available it is preferable to use a diode laser because it presents very narrow spectral width (width of the emitted line smaller than 30 MHz) together with a wide tuning interval (about 6 nm for the laser used for carbon dioxide determination). Among the more apt laser it is preferred a diode laser with vertical cavity (VCSEL). Other possible lasers can be: DFB laser, Fabry-Perot laser, SePb laser and Quantum Cascade Laser. In a VCSEL laser the wavelength can be tuned by varying the temperature or the current of the laser. Providing one or both of these quantities varying in time allows to have a tuning along the absorption line of the gas under examination. For obtaining the absorption spectrum the current flowing on the laser is modulated with a sawtooth or triangular wave at the frequency of some hundredth Hz, as shown in FIG. 3. These wave shapes are optimal for extracting the parameters of interest in the easiest way but it is possible to use also other shapes of waves as e.g. sinusoidal, provided that they provide the laser with a current continuously variable between two fixed values. In FIG. 3 it is shown the laser source 6, the container 8, the detector 10, two lenses 16 one collimating and one collecting, a current modulator 18, a temperature controller 20 and a computer 22. The current modulator 18 is connected to a rump generator 24 and it is able to modulate the laser current as required. The computer 22 is used for manipulating the data measured by detector 10 for an easier handling. Computer 22 can be substituted by a microprocessor or DSP for data analysis that allows the A/D conversion and numerical computation.

The method adopted in this invention is the direct absorption known as TDLAS: Tunable Diode Laser Absorption Spectroscopy. In some cases, due to the very low value of the molecular cross-section $\sigma(v)$ it is necessary to use derivative spectroscopy know as: WMS (Wavelength Modulation Spectroscopy) or FMS (Frequency Modulation Spectroscopy) (Frequency-modulation spectroscopy for trace species detection: theory and comparison among experimental methods. Applied Optics, Vol. 31, Issue 6, pp. 707- February 1992 Joel A. Silver) in which at the described modulation it is added a sinusoidal modulation at frequency of some MHz.

This method is particularly useful for the detection of oxygen inside wine bottles, particularly of red wine where it is required a constant control of the oxygen concentration in the head space that is the space of container 8 near the closing cork. An increase of the oxygen concentration could be due to transfer from the dissolved oxygen and could be a sign of a deterioration of the product. Since both the concentration of the oxygen to be detected as well the absorption cross section are small it is necessary to increase the sensitivity of the measure using derivative spectroscopy. In the case of oxygen the preferred laser is a VCSEL at 760 nm. Even in the case of oxygen a known method is used but new procedures of data analysis and determination of pressure and concentration are defined in such way as to allow precise measurements even for high pressures and without the need to have reference paths or the need to know a priori the optical characteristics of the container.

In order to realize a portable device microsystems and miniaturized sub-systems have been used with the purpose of obtaining a whole package of reduced dimensions and easily applicable to several types of containers 8. The central element of the measuring system is as already said the VCSEL laser or any other laser that presents the same characteristics in terms of wavelength of emission and possibility of modulation. Said laser is mounted in a suitable mounting with fine temperature control using a thermistor associated to a Peltier cell capable of keeping constant the temperature with an accuracy of 0.01° C. The mount of laser 6 is provided with necessary connections for connecting the VCSEL with the current modulator 18 and with the temperature controller 20. The latter are electronic devices that allow the operator to set and maintaining the temperature and current values provided to the laser 6. A laser of this type presents a line width smaller than the traditional laser diodes: the VCSEL utilized for the water vapour measurement has a line width with a typical value of FWHM (Full Width at Half Maximum) of 30 MHz and the one used for carbon dioxide has a width slightly more. This characteristic is very important in spectroscopy; using this property it is possible to obtain a precise scan and a reliable measure of the absorption line whose width is several order of magnitude larger (the estimated width for standard temperature and pressure values is about 7 GHz for both water vapour and carbon dioxide). Furthermore a VCSEL is a nearly monomode laser: in effect its SMSR (Side Mode Suppression Ratio) presents values that varies from 30 to 60 dB; this means that the side modes give a negligible contribution to the laser emission and therefore can be neglected.

Detector 10 used in this measuring system is preferably a preamplified photodiode. Detector 10 varies according to the laser used: for water vapour photodiodes of Germanium or Indium Gallium Arsenide (InGaAs) can be used while in the case of carbon dioxide extended InGaAs, or Lead Selenide (PbSe) or PbS photoresistors can be used (Peter Werle, Franz Slemr, Karl Maurer, Robert Kormann, Robert Mücke, Bernd Jänker, Near- and mid-infrared laser-optical sensors for gas analysis, Optics and Lasers in Engineering 37 (2-3), 2002, pp. 101-114).

The electronic following detector 10 not shown in the figures provides an output proportional to the absorbance at the given wavelength. The absorbance provided by a numerical computation realized by computer 22 can be translated in gas concentration as explained in the following.

Now we enter in detailed description of the measure of the pressure and concentration of the gas in the container. These quantities are strictly related to the measure of amplitude and width of the absorption line. In fact if one neglects (or deconvolve) the contribution to the line width of Doppler effect, it is known that the line profile given by a Lorentzian shape has a width directly proportional to the pressure of the gas. This means that, by measuring the width at half maximum one can derive a measure of the pressure inside the container. In similar way the gas concentration (being it carbon dioxide, oxygen water vapour or other) is related to the amplitude of the absorption line; if one compares the height of the experimentally measured line with the height of the same line at known concentration and pressure one derives the concentration.

When measurements of absorption lines are made with a system like the one shown in FIG. 1 there are typically three factors that affect such measure: the nature and shape of the walls of container 8, the pressure inside said container 8 and the contribution due to the gas present in the path external to the container 8. The nature and shape of the walls of the container produce an attenuation of the absorption spectrum not known a priori; the pressure inside the container produces a broadening and eventually a merging of the lines and the external absorption introduces an error in the measure. In addition, particularly when using lasers with narrow width of the line i.e. with high temporal coherence, there could be etalon effects due to reflection on the various optical surfaces. Etalon effect produces noise.

In the following we describe example of analysis of the absorption spectra for water vapour and carbon dioxide. For the case of water vapour is particularly important the contribution due to the path external to container 8. The same case applies also to the analysis of oxygen. For the case of carbon dioxide we consider instead the contribution due to the internal pressure and the one due to the nature and shape of the container 8 and neglect the contribution due to the path external to container 8 since the concentration of carbon dioxide in air can be neglected with respect to the one present e.g. in a bottle of sparkling wine or beer. Off course it is possible to consider simultaneously all three effects independently of the gas analyzed.

Figure 4A:
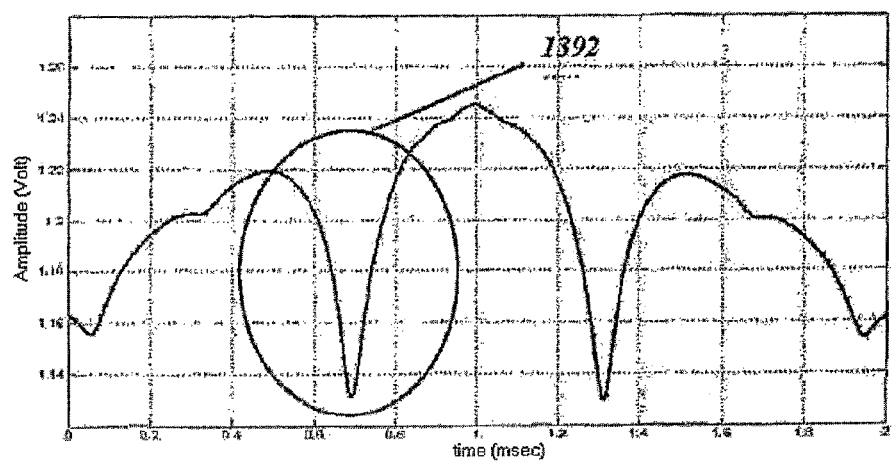
FIGS. 4(A) through 4(B) show two examples of signals recorded by the measuring system.
Figure 4B:
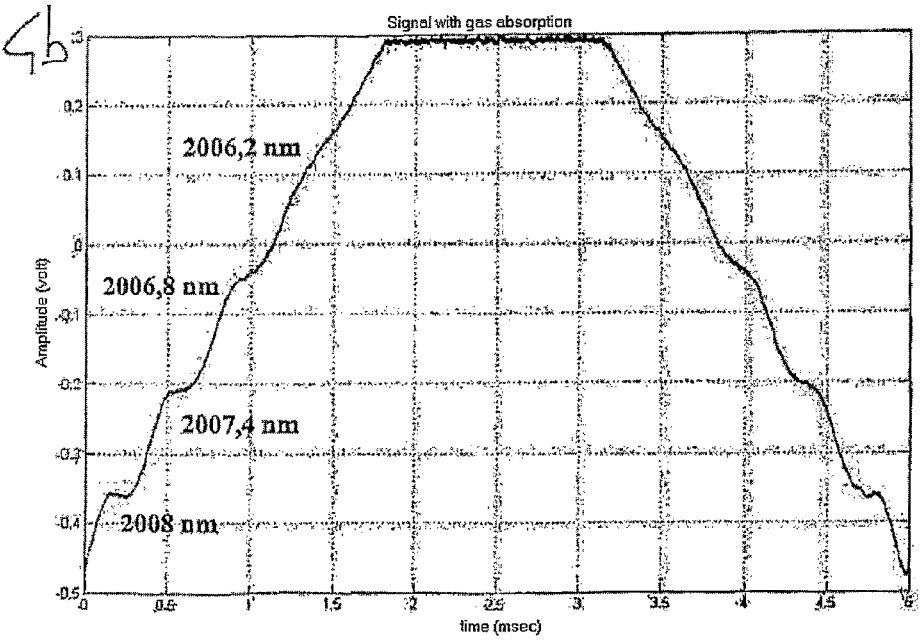

In FIGS. 4a and 4b two examples of the signals acquired by detector 10 are shown: from these it is apparent that it is necessary to perform a numerical computation of the said signal in order to derive the required values of amplitude and width of the lines. In the first, FIG. 4a it is shown a signal of water vapour and in the second: FIG. 4b the absorption lines (shown upside down since in this case the detector 10 is with a preamplifier in inverting mode) are due to carbon dioxide in a sparkling wine bottle. In both cases the wavelengths at the centre of the lines are indicated. In these figures and in particular in the case of the carbon dioxide, it is clear that both the presence of the rump modulating the intensity of laser 6 as well the interaction among nearby lines do not allow the precise determination of either the amplitude and the width of the lines.

Figure 5:
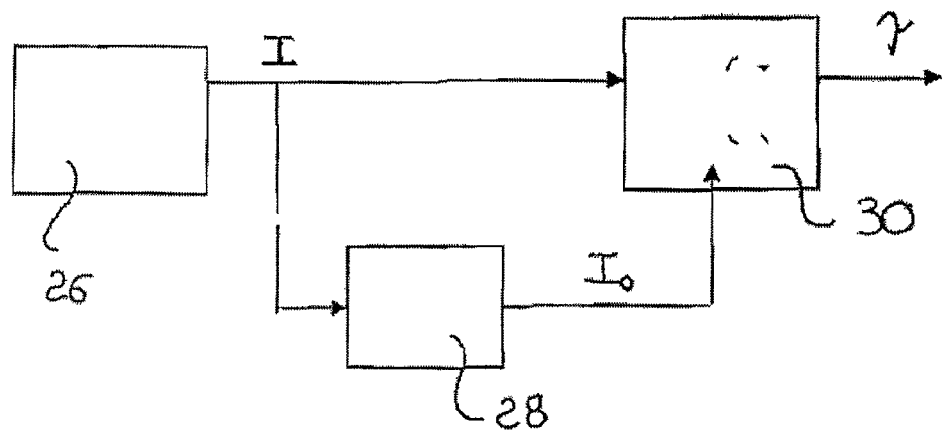
FIG. 5 is a schematic diagram showing the method for eliminating the modulating ramp.

One of the purposes of the present invention is the development of a specific computational method for eliminating the modulating signal and to obtain the required parameters of the absorption lines even in the presence of high pressures and consequently of merged lines as well to discriminate between the background introduced by the glass of the container and the "atomic" background due to the merging of the lines. The first step of the analysis is the elimination of the modulating rump; for doing this operation the procedure illustrated in FIG. 5 is performed. The scheme of FIG. 5, based on the Lambert-Beer law is composed of a block 26 that acquires the trace provided by detector 10 and provides measured intensity I. Said intensity I is input to block 28, a computer unit that provides an evaluation of the intensity $I_0$ incident on the analyzed sample. The way to accomplish this depends on the gas to be analyzed and on the measure that is required; in any case it is required to obtain the behaviour of the rump in absence of the absorption. Once obtained an approximation of the signal without absorption, the two traces (I that is the trace with absorption and $I_0$ that is the trace without absorption) are compared and using Lambert-Beer law one derives the effective absorption line (or lines) profile. The latter comparison is performed by block 30, another computing block that outputs the absorption profile that is function of the wavelength and of the optical depth τ according to the expression:

$$\tau(x,v) = \log_e [I_0(v)/I(x,v)] \quad (3)$$

Taking x as the length of the optical path inside the container, it is clear that by comparing the intensities of the beam before and after the optical path one derives the quantity τ. Block 28 and 30 can be integrated in the computer 22. However as previously indicated there are situations in which it is necessary to modify somehow the model for the analysis. In the case of water vapour one needs to account also of the contribution to absorption due to the path external to container 8. This correction can be obtained analytically using a suitable spectroscopy data base or can be obtained experimentally if one acquires a signal in free space: in this case in effect the absorption refers to know conditions (atmospheric pressure and relative humidity measurable with precision).

Figure 6:
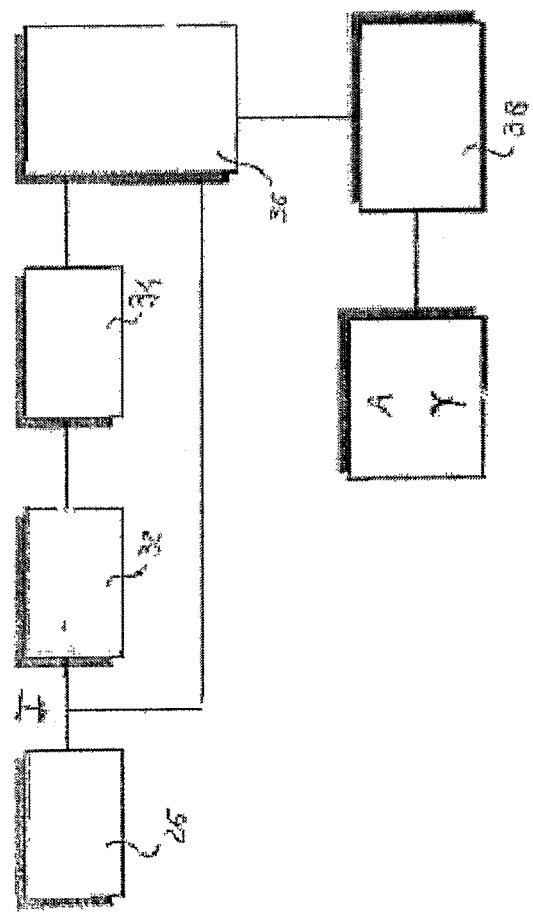
FIG. 6 shows one example of the best fitting of the Lorentzian profile for the lines of water vapour.

The evaluation of the trace without absorption is derived from the experimental signal neglecting the regions where there are absorption lines and fitting the rest with a third order polynomial interpolation. This can be explained with reference to FIG. 6. In this figure 26 indicates the block that acquires trace I and sends the signal to block 32 which eliminates the regions containing the lines. Block 34 executes a polynomial interpolation of the signal. Block 36 now compares the initial trace I and the signal output from block 34 and output the absorption lines. Finally block 38 compares the Lorentzian profile corresponding to the absorption lines as given by block 36 with a reference Lorentzian profile at atmospheric pressure and provides the parameter of the unknown Lorentzian i.e. amplitude A and line width $\gamma$. All blocks 32, 34, 36 and 38 representing computing units can be incorporated in computer 22.

Figure 7:
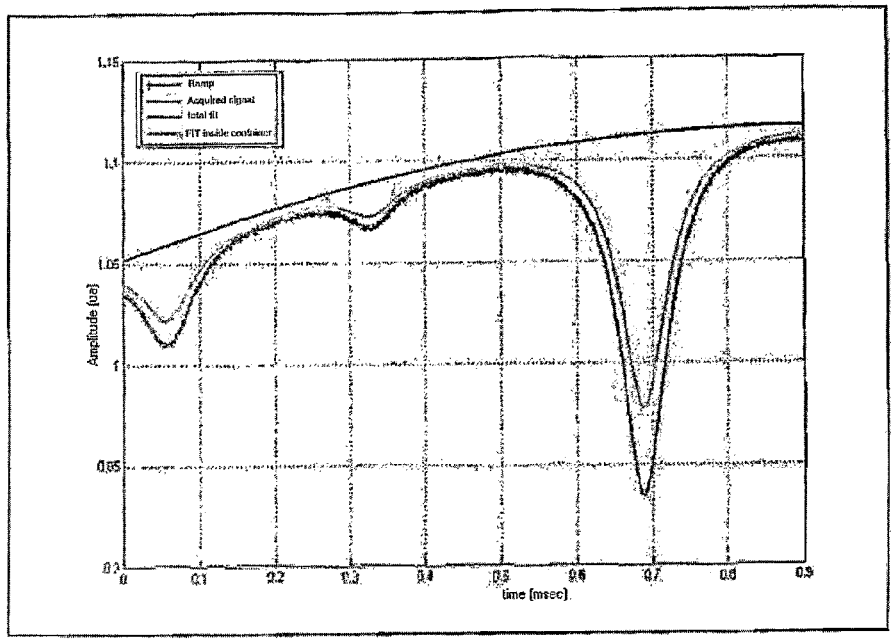
FIGS. 7 and 8 show two polynomial fittings of the lines for the case of water vapour and pressure of 1 and 5 bar.
Figure 8:
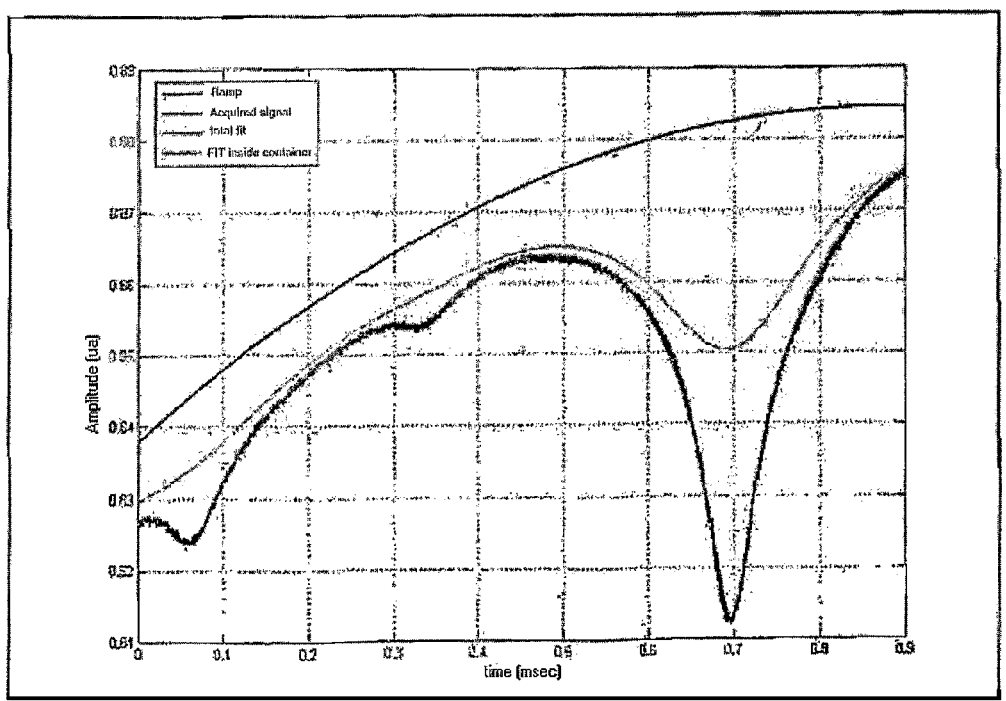
Figure 9:
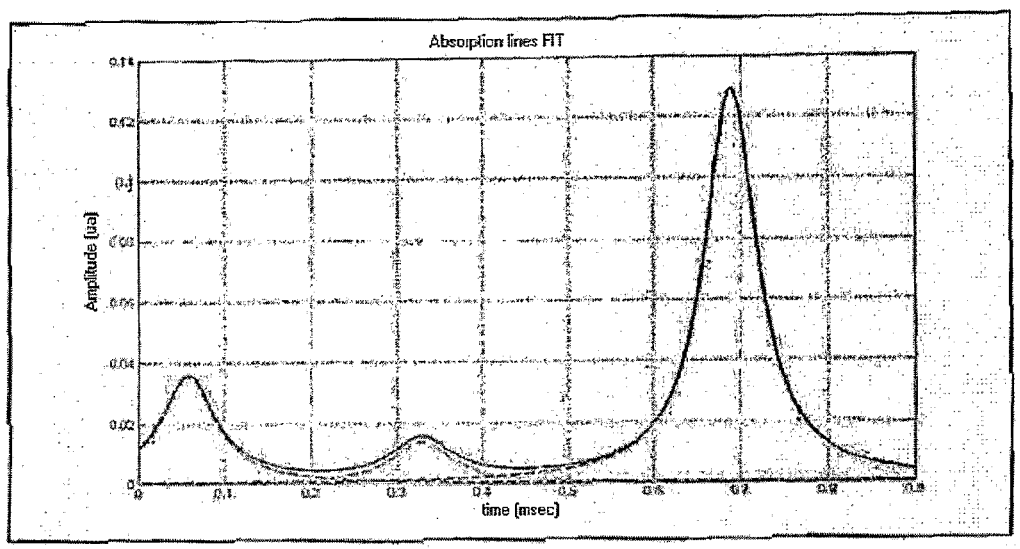
FIGS. 9 and 10 show the corresponding absorption lines of water vapour for the cases of FIGS. 7 and 8.
Figure 10:
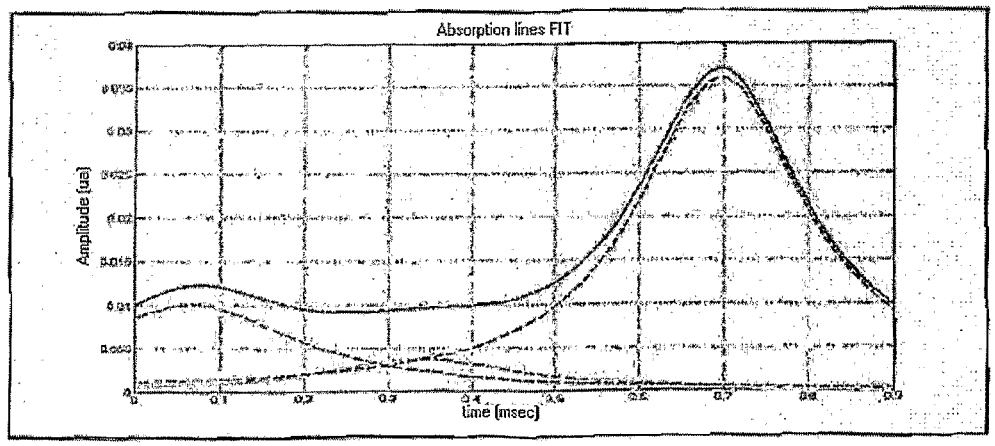

Taking in account the absorption external to container 8 one obtains the graphs shown in FIGS. 7 and 8 respectively at pressures of 1 and 5 bar. Form these graphs one obtains the absorption lines of the water vapour present in the bottle as indicated in FIGS. 9 and 10 in which with dotted lines are shown the single lines and with solid lines the total absorption by the water vapour present inside the bottle. Having now obtained the absorption lines it is possible to determine the FWHM and consequently with the help of computer 22 values of gas pressure and concentration inside the container as previously explained.

In the case of carbon dioxide distortion in the absorption spectra due to the nature and shape of the wall of the container (including wall defects such as blisters and cracks) as well as the gas pressure have to be considered. These issues produce a spectrum with very merged absorption lines and this makes very difficult the determination of the modulating rump with the previously described method, particularly when the pressure of the gas is high. The carbon dioxide absorption spectrum, used for this described analysis, is made up of two regions as shown in FIG. 2 consisting in several lines. Some of these lines are quite near each other; so if the gas pressure increases, so does the FWHM of the lines. This line broadening could eventually be very strong and the lines become so merged that not only their profiles but also the total absorption contribution, and its parameters cannot be determined.

Figure 11:
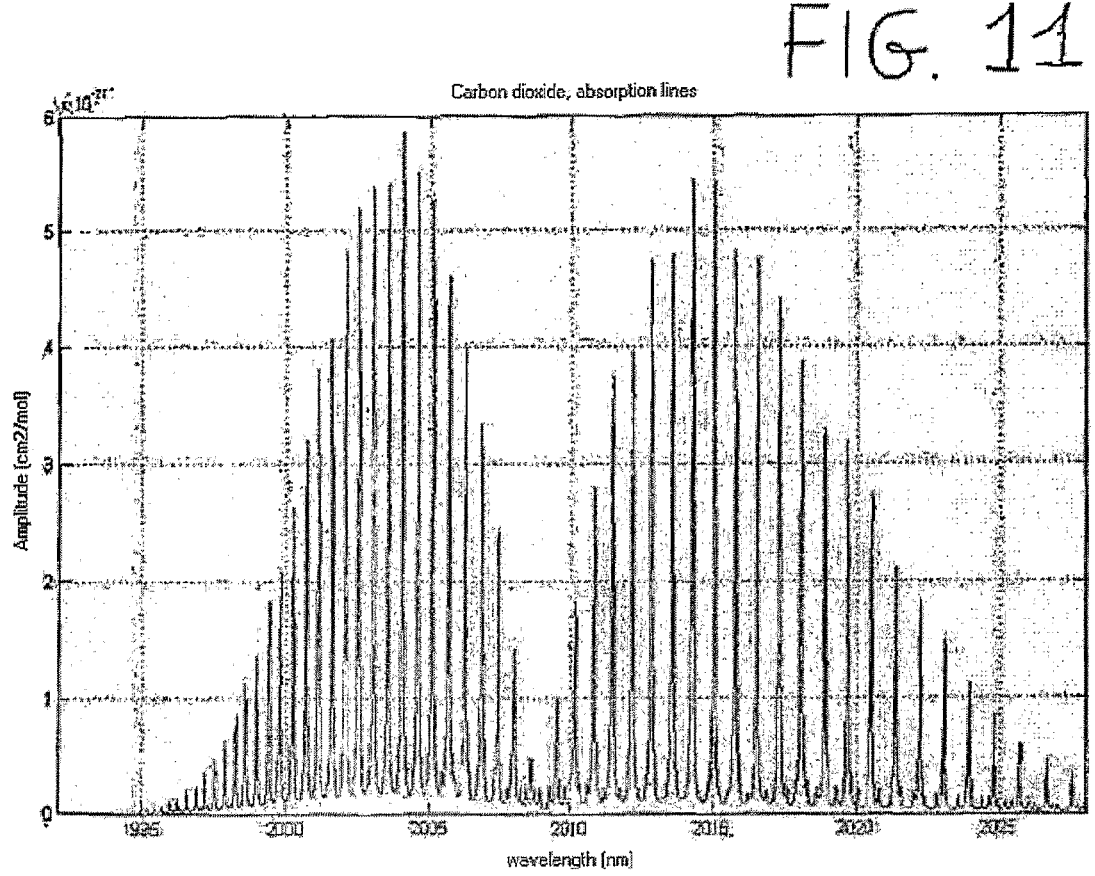
FIGS. 11 and 12 show absorption spectra of carbon dioxide at 1 and 7 bar in the same wavelength interval.
Figure 12:
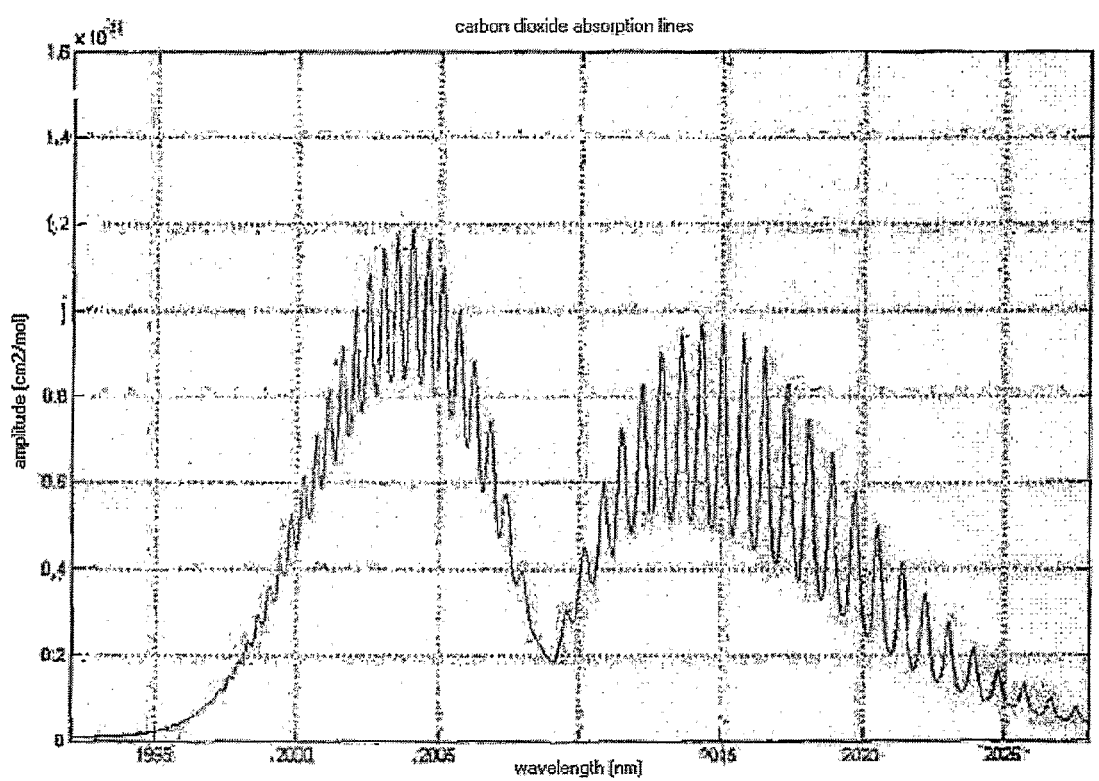

FIGS. 11 and 12 show the same lines spectrum at the pressures of 1 and 7 bar; the merging of the lines in the latter case is evident as well as an apparent background over which the lines appear. This "atomic" background is the main problem for obtaining a precise fit reconstruction. In effect this "atomic" background couples with the background due to the absorption and scattering by the glass walls of container 8. The latter effects being not known a priori because e.g. the wine bottles to be measured could be of any type and quality and there is not the possibility to determine their background in a separate measure. In order to solve these problems, the processing device (22) operates the measurement of the amplitude of the signal and selects a proper optimal background shape from a database of background analytic functions which better fits with the selected glass container. This customizable database can be realized selecting different kinds of glass containers according to the application.

The algorithm in turn interpolates this selected background function with a third grade polynomial fit. The output of this step are four coefficients representative of the background.

Furthermore, based on the Lambert-Beer law, the processing device (22) performs an operation of polynomial-exponential fit using the following expression:

$$[A + Bt + Ct^2 + Dt^3]\exp\left\{-\sum_i \frac{\gamma_i A_1}{\gamma_1^2 + (t - t_i)^2}\right\} \quad (4)$$

Figure 13:
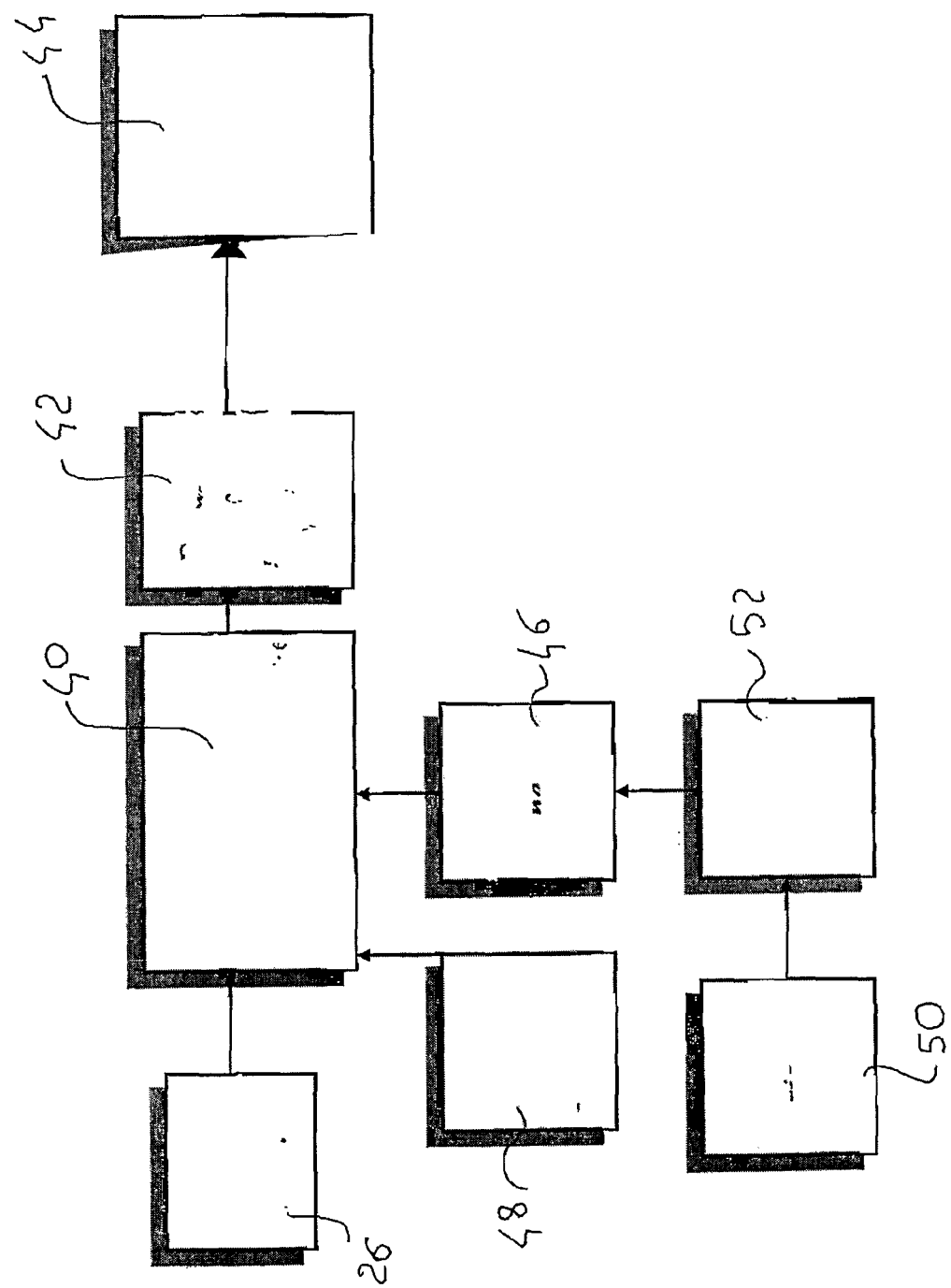
FIG. 13 is a schematic diagram showing the procedure for fitting the lines for the case of carbon dioxide.

A,B,C,D are the coefficients of the third grade polynomial background and the coefficient starting values were those obtained in the previous step;

the absorption lines (whose shapes are expressed inside the sum) whose parameters (HWHM: $\gamma$, amplitude: A and line center position: $t_i$) are unknown and are determined by a best fit procedure as described later. The number of lines included in the model is variable and depends on the power and duration of the computation; for getting good results it is important to include all the lines in the absorption region of interest that, increasing the pressure, contribute to the chosen measuring interval. In the case of carbon dioxide there are approximately 20 "side" lines that at the maximum pressure considered (8-10 bar) interact with the chosen measuring spectral region. In FIG. 13 is shown the block scheme for the computation performed in the case of carbon dioxide scheme that is valid for any gas with absorption lines very near each other. Block 26 acquires signal I and outputs to block 40 that performs the polynomial-exponential fit according to equation (4). The purpose is to determine the coefficients of the third degree polynomial and the unknown parameters present in the exponential. The coefficients of the polynomial are calculated by best fitting a polynomial on trace I and choosing arbitrary coefficients for the polynomial. The unknown parameters of the exponential are determined according to interpolation parameters 48 derived from a spectroscopic data base as e.g. Hitran (The HITRAN 2004 molecular spectroscopic database, L. S. Rothman, D. Jacquemart, A. Barbe, D. Chris Benner, M. Birk, L. R. Brown, M. R. Carleer, C. Chackerian, Jr, K. Chance, L. H. Coudert, V. Dana, V. M. Devi, J.-M. Flaud, R. R. Gamache, A. Goldman, J.-M. Hartmann, K. W. Jucks, A. G. Maki, J.-Y. Mandin, S. T. Massie, J. Orphal, A. Perrin, C. P. Rinsland, M. A. H. Smith, J. Tennyson, R. N. Tolchenov, R. A. Toth, J. Vander Auwera, P. Varanasi, and G. Wagner, J. Quant. Spectrosc. Radiat. Transfer 96, 139-204, 2005) that provides distance between lines, relative intensity of the lines, relative widths of the lines etc.

At this point block 42 outputs the parameters $A_i$ and $\gamma_i$ of the Lorentzian corresponding to the absorption lines from which block 44 derives the values for the pressure and concentration.

An alternative to the model is to impose in the determination of the coefficients of the polynomial a correction of the rump 46. The third degree polynomial is compared with a rump acquired in free space (obtainable by acquiring the signal in absence of container 8) multiplied by a coefficient K that takes into account the attenuation introduced by the container. The formula that can be applied is the following:

$$f(t) = K(Ramp_{Freespace})\exp\left[-\sum_i L_i\right] \quad (5)$$

where $L_i$ are the unknown Lorentzians.

The justification for applying expression (5) stays in the fact that a beam that traverses a partially transmitting window is only attenuated maintaining constant its shape; possible small perturbation of the shape can be corrected during the computation.

Block 46 that performs the comparison receives as input the trace acquired in free space 50 and block 52 performs the polynomial interpolation according to relation (5).

Another alternative way of determining the background due to the container 8 is to use an additional laser (not shown in the Figures) collinear to laser source 6 whose wavelength is outside the absorbing band of the gas to be measured. The beam of the latter laser is therefore attenuated only by the container 8 and not by the gas. By measuring the intensity of the latter laser one derives the background due to the container and this information can be inserted in the process of calculation e.g. as input to block 40.

All blocks form 40 to 52 previously mentioned represent computational units and can be integrated in computer 22. Once available the values for the parameters describing the lines (HWHM, centre of the line and peak value) it is possible to derive from these the values for the pressure inside the container as well the concentration of the gas as a partial pressure of the said gas. The total pressure is derived from the relation:

$$P_{total} = \frac{Centerline(Hitran) \cdot HWHM(experimental)}{Centerline(experimental) \cdot HWHM(Hitran)} \quad (6)$$

Once determined the total internal pressure, the partial pressure of the gas can be determined with the following procedure; this quantity is related to the concentration of the said gas in the container. If we indicate with:
  $\tau$ the value of the peak of the absorption line as measured
  p the total internal pressure
  $\gamma$ the theoretical width of the line related to collisions with the gas molecules
  S the theoretical total area of the line profile
  L the length of the optical path in the container
  $N_l$ the Loschmidt number Than the partial pressure is derived from the following equation:

$$p_{partial} = \frac{\tau \cdot p \cdot \pi \cdot \gamma}{S \cdot l \cdot N_l} \quad (7)$$

In this way the amplitude, the widths and the values for the centre line of the various lines (that are related by constant and known ratios among themselves) as well as the attenuation due to the container are determined.

Now we have applied the procedures previously described for the measure of pressure of water vapour and carbon dioxide in several containers, using a laser at 1390 nm or one at 2004 nm according to the gas present.

Figure 14:
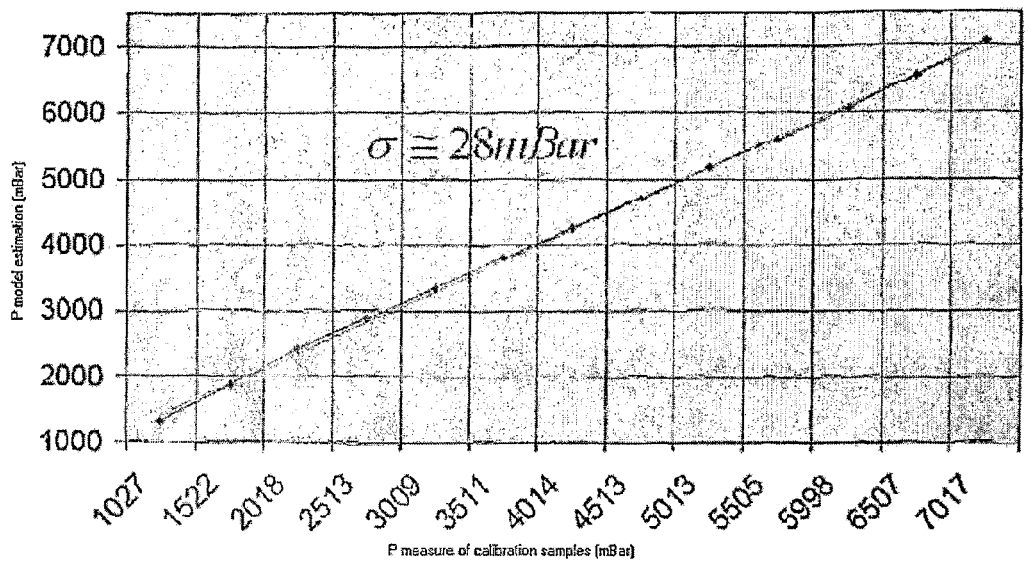
FIG. 14 is one example of curve of calibration.
Figure 15:
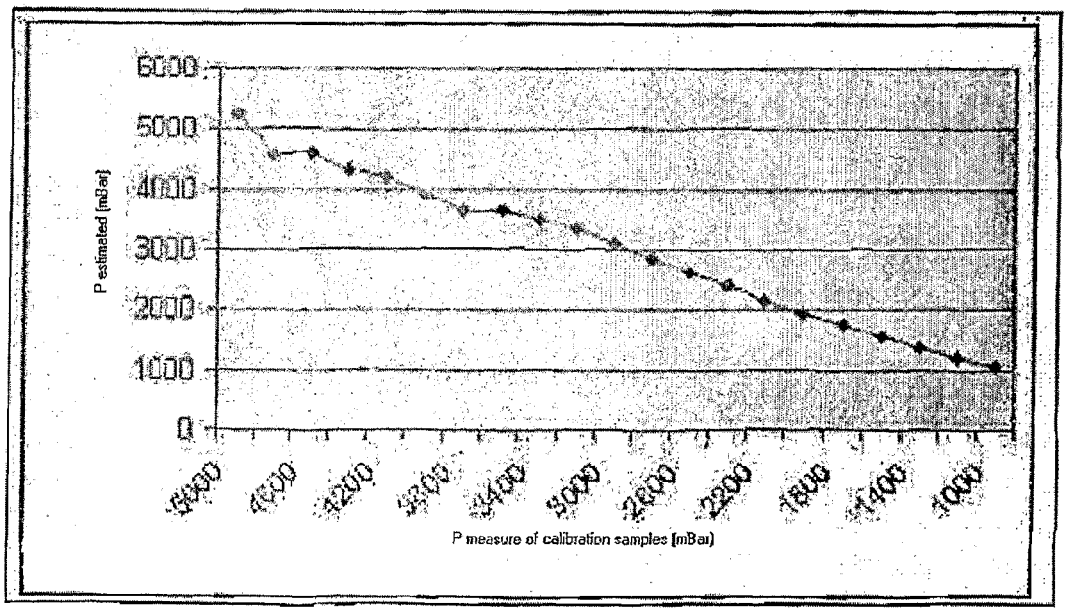
FIG. 15 show a graphical representation of the pressure measurement applied to mineral water bottles.

A measure that is particularly relevant is the one performed on wine bottles as a knowledge of the pressure is related to the characteristics of the same wine and in particular its position on the marked discriminating between sparkling and champagne; furthermore knowing the pressure with small uncertainty allows to certify the product and some of its proprieties. The measuring system has been calibrated using tests containers with known internal pressure and concentration (e.g. pressure between 1 and 7 bar with steps of 50 mbar). The calibration curve is shown in FIG. 14 while in FIG. 15 are reported measured values of pressure in the case of bottles of mineral water.

Pressure measurements present good reproducibility and sensitivity with a sigma value with respect to the polynomial interpolation of 28 mbar. The measured values appear slightly overestimated but the apparatus can be better calibrated using a look-up table.

As can be appreciated, even if the invention is described with particular relevance for the sector of bottling in the beverages field (water, wine, beer), it can be applied to any field provided the container is even partially transmissive to the wavelength of the laser.

Of course without loss of validity the ways of realizing the device and the details could be amply varied with respect to what described that is realized as a mere example not limitative without for this to escape from the field of the invention as better described in the annexed claims.

The invention claimed is:

1. A method for measuring pressure and/or concentration of a gas in an optically transparent container with unknown and variable background spectrum, using a system for automated measuring of total gas pressure and of partial pressure of one selected component of a gas in at least partially optically transparent closed containers; said containers being of different types, such as bottles of glass or plastic material whose sidewall surfaces have an intrinsic transmission totally un-known and variable from one type to another within a very large range, in which the system includes:
  a laser source which emits a laser beam of a predetermined wavelength, towards the optically transparent closed container which contains the gas to be measured, said gas partially absorbing the wavelength of the laser beam
  optical detectors configured to detect the laser beam which is attenuated by the gas absorption; wherein said detectors provide first data of gas absorption representative of a first absorption spectrum of the gas including distorted absorption lines and background absorption due to the container walls and noise
  an implemented method which is a feature of the calculation and processing device for recording and elaborating said first data; wherein the output of these operations are parameters which represent a second absorption spectrum free of distortion in the absorption lines and of the background; from these parameters it is possible to determine gas pressure and concentration in the container;

the method comprising the actions of:
  applying a suitable background subtraction algorithm which eliminates the spectral contributions other than the contributions due to the gas absorption from the first data; and
  measuring an amplitude of a signal at the detector, the processor selecting, from a database, not a fixed polynomial baseline, but a pseudo-background function (characterized by four polynomial coefficients A; B; C; D), the coefficients being an input initialization for the polynomial coefficients for a real-baseline obtained at a next step, so that a new fit will work only for a bounded range of values with well-defined constraints.

2. The method of claim 1, further comprising the actions of:
  executing a polynomial-exponential fit of the data of the spectrum according to the following formula:

$$K \cdot [A + Bt + Ct^2 + Dt^3] \exp\left\{-\sum_i \frac{\gamma_i A_i}{\gamma_i^2 + (t - t_i)^2}\right\}$$

wherein K is a coefficient which considers the glass attenuation; A, B, C, D are coefficients of a third grade polynomial background and the coefficient starting values; and wherein absorption line parameters include HWHM: $\gamma$, the amplitude: A and the line centre position: $t_i$; in which all such parameters are determined employing a best fit procedure; and depending on a range of pressure and on a merging between different absorption lines, an exponential sum goes up to 20 side lines.

3. The method of claim 1, further comprising the action of: determining the absorption by HWHM and the centreline; in which total pressure and concentration are obtained with the following formula:

$$P_{total} = \frac{Centerline(Hitran) \cdot HWHM(experimental)}{Centerline(experimental) \cdot HWHM(Hitran)}$$

where Hitran indicates parameters from the spectroscopic data base Hitran and "experimental" indicates values obtained with a best fit operation.

4. The method of claim 1, further comprising the action of: calculating the partial pressure of the gas in the container with a formula as follows:

$$p_{partial} = \frac{\tau \cdot p \cdot \pi \cdot \gamma}{S \cdot l \cdot N_l}$$

$\tau$ being a value of a peak of the absorption line as measured, p being a total internal pressure, $\gamma$ being a theoretical width of the line related to collisions with the gas molecules, S being a theoretical total area of the line profile, L being a length of the optical path in the container and $N_1$ being a Loschmidt number.

5. The method of claim 1, further comprising the action of: employing a back reflecting optic to reflect the beam coming from a light source and the container, wherein the light source and a detector are positioned in a same side with respect to the container.

6. The method of claim 1, further comprising the action of disposing, between the laser source and the container, at least one lens for collimation and focalization and reducing an optical path in free space in order to minimize absorption and correcting optical aberrations introduced by the container.

7. The method of claim 1, further comprising the action of employing a current driver modulator and a temperature controller.

8. The method of claim 7 where the current driver has a triangular-shaped or sawtooth-shaped modulation or a combination of triangle- and sine-modulation.

9. The method of claim 1, further comprising the action of choosing the wavelength of the laser beam in accordance with the absorption characteristics of the gas to be detected; wherein, in case of high pressure producing line broadening, line merging effects and a mixing with the background due to the sidewalls of the container, lines positioned at the edges of the absorption branches are detected by the optical detectors.

10. The method of claim 1, wherein the laser source includes Vertical Cavity Surface Emitting lasers (VCSELs).

11. The method of claim 1, wherein the optical detectors include pre-amplified photodiode or photo-resistors.

* * * * *